United States Patent [19]
Treiber

[11] Patent Number: 5,287,856
[45] Date of Patent: Feb. 22, 1994

[54] FOCAL RANGE LOCATING SYSTEM FOR LITHOTRITY

[75] Inventor: Jobst Treiber, Munich, Fed. Rep. of Germany

[73] Assignee: Dornier Medizintechnik GmbH, Munich, Fed. Rep. of Germany

[21] Appl. No.: 874,761

[22] Filed: Apr. 27, 1992

[30] Foreign Application Priority Data

Apr. 26, 1991 [DE] Fed. Rep. of Germany ....... 4113697

[51] Int. Cl.$^5$ .............................................. A61B 17/22
[52] U.S. Cl. ............................ 128/660.03; 128/241 L
[58] Field of Search ....................... 128/24, 66, 660.03

[56] References Cited

U.S. PATENT DOCUMENTS 4,580,894 4/1986 Wojcik .
4,962,754 10/1990 Okazaki ........................... 128/660.03
5,065,741 11/1991 Uchiyama et al. .............. 128/660.03
5,174,294 12/1992 Saito et al. ...................... 128/660.03

FOREIGN PATENT DOCUMENTS 0367116 5/1990 European Pat. Off. .
0377901 7/1990 European Pat. Off. .

*Primary Examiner*—Ruth S. Smith
*Attorney, Agent, or Firm*—Evenson, McKeown, Edwards & Lenahan

[57] ABSTRACT

This invention relates to a system for locating the focal range for extracorporeal shockwave lithotrity. Motion in the patient's body induced by the shockwaves are detected by a comparison of several ultrasonic B-scan-images taken with a time delay. The detected processes of motion are displayed on a video screen by means of color coding.

4 Claims, 3 Drawing Sheets

FOCAL RANGE LOCATING SYSTEM FOR LITHOTRITY

BACKGROUND AND SUMMARY OF THE INVENTION

This invention relates to a system for locating the focal range of shockwaves generated by a shockwave source relative to a concrement situated in the body of a living being.

The ESWL (extracorporeal shockwave lithotrity) focal range may, particularly under anatomically unfavorable conditions, deviate considerably from the theoretical geometrically determined focus. Thus, exact positioning of the concrement to be treated is not possible in such cases, and the ESWL effectiveness is correspondingly low. Direct imaging of the shockwave propagation/focusing in the body cannot be carried out by means of the imaging methods known in the field of medicine.

In the apparatus disclosed in European Patent Document EP 367,116, the focal range is located indirectly by detecting motion in the body induced by the shockwaves. The ultrasonic Doppler process used in this device, however, measures only the radial speed with respect to the ultrasonic scanner from which the ultrasonic waves originate, and by which their echoes are received.

It is an object of the present invention to provide a system by means of which the focal range of the shockwave source can be reliably located, so that the concrement can be securely positioned in the focal range.

According to the invention, this object is achieved indirectly by detecting motion induced by the shockwaves, in the stone material, in the fluid surrounding the concrement or in the body tissue. (Another possibility is the movement of cavitation bubbles generated in the shockwave field.) Since such motion is most pronounced in the focal range, location of this region is possible.

The detection of induced motion in the interior of the patient's body takes place non-invasively by interpretation of an ultrasonic B-scan-image (also called simply a "B-scan-image"), used for the ESWL-locating of the stones. Such movements are detected by segmenting and correlating successive B-scan-images, in a device for the detection of the motion induced by the shockwaves. The comparison is not limited to images that follow one another directly ($B_i$, $B_{i+1}$), but advantageously, also permits comparison of images $B_i$, $B_{i+k}$, where $k > 1$. The determined speed values are used to generate a color-coded speed pattern, which may be superimposed on the ultrasonic B-scan-image.

In the case of such a speed pattern, a color/intensity combination is assigned to any combination of the amount/speed.

Imaging errors due to refraction and diffraction of sound inherent to the B-scan-image in this case do not have any effect on the location of the focal range, because the position of the focal range relative to the concrement is decisive for the ESWL-positioning.

Other objects, advantages and novel features of the present invention will become apparent from the following detailed description of the invention when considered in conjunction with the accompanying drawings.

DETAILED DESCRIPTION OF THE DRAWINGS

Figure 1A:
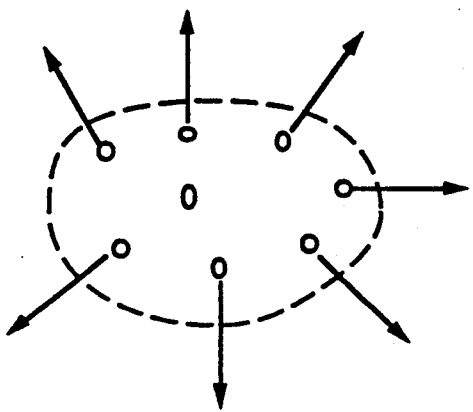
FIGS. 1 $a$-$c$ depict schematically the processes of motion in the body induced by the shockwaves.
Figure 1B:
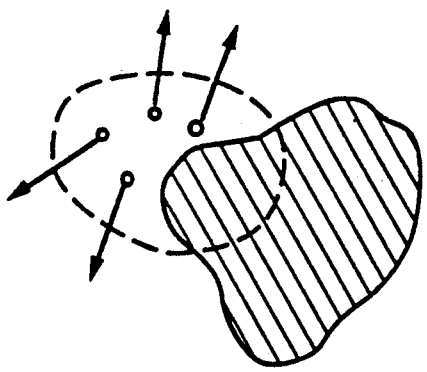
Figure 1C:
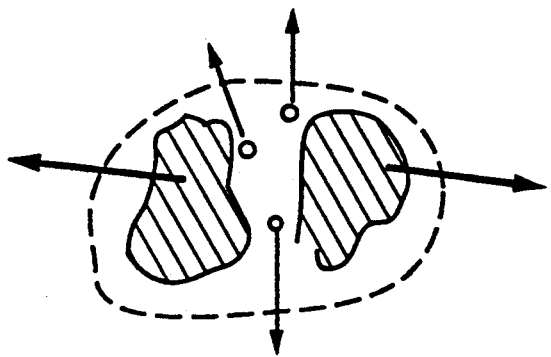

FIG. 1$a$-1$c$ schematically illustrates the movements induced by shockwaves used to locate the focal range, which in each case has a border consisting of an interrupted line. (The directions of the movements are indicated by arrows.) FIG. 1$a$ represents the dynamics of cavitation bubbles created in a fluid within the focal range of the shockwaves. Such cavitation bubbles act as a moved ultrasonic contrasting medium, and are therefore visible in the ultrasonic B-scan-image. FIG. 1$b$ represents the dynamics of stone material within the focal range. Large stones such as shown in FIG. 1$b$ act essentially immobile so that mainly the cavitation bubbles forming in the surrounding fluid are used to locate of the focal range. In FIG. 1$c$ the dynamics of stone fragments are shown. In this case, the movement of the stone fragments as well as the cavitation bubbles formed in the surrounding fluid are suitable for locating the focal range.

Figure 2:
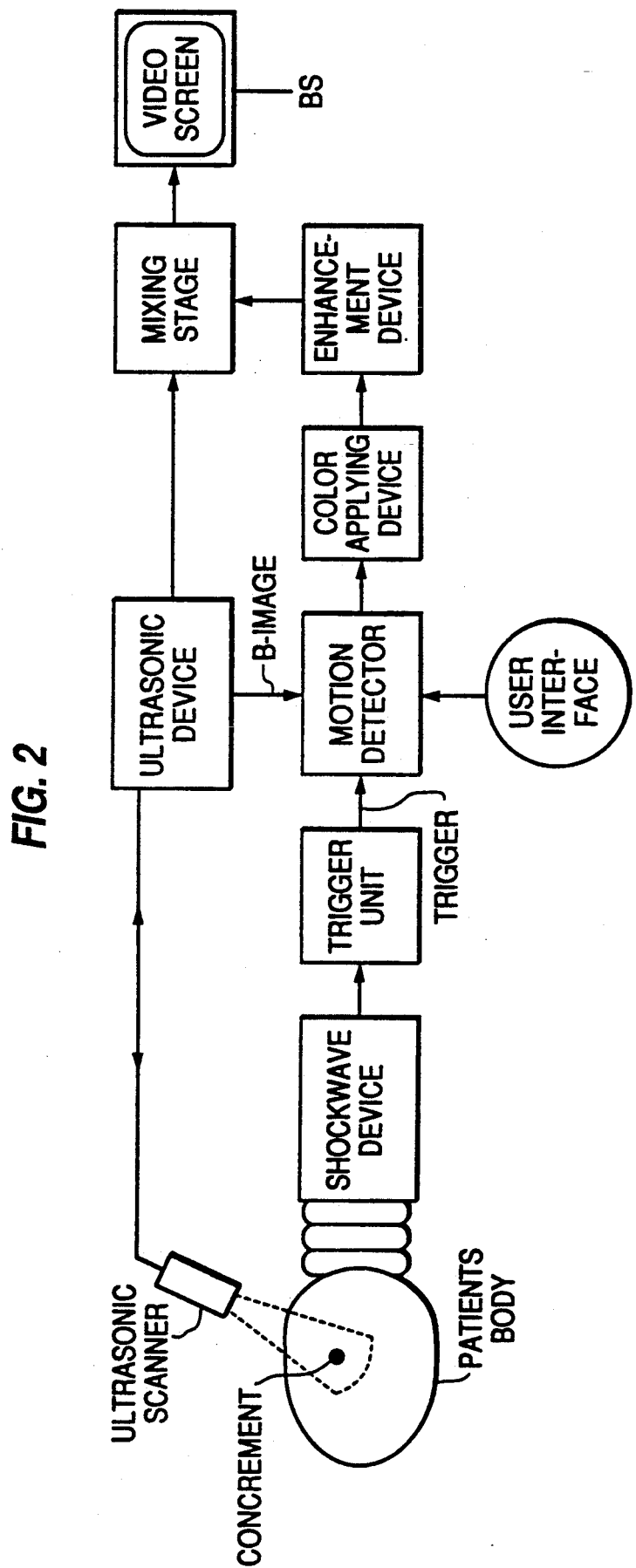
FIG. 2 is a block diagram of an arrangement according to the invention.

FIG. 2 is a block diagram of a system according to the invention. Concrement K to be treated is situated in the patient's body PK. In the shockwave source SQ, ultrasonic shockwaves are generated, focussed and aligned with the concrement K. An ultrasonic scanner SC, a commercially available standard medical imaging device (high resolution) having a typical frequency range of 3-5 MHz, emits ultrasonic waves and receives their echoes, which are processed in the ultrasonic device US into an ultrasonic B-scan-image of the body area to be viewed. The B-scan-image is transmitted to a motion detector device BD for detection of motion induced by the shockwaves. (The device BD may be, for example, an image processing system including a 486 processor, 33 MHz, with DOS 5.0 operating system, programming language C.) There, the detection takes place, as described hereinafter, by segmentation and correlating of two B-scan-images $B_i$. $B_{i+k}$ ($k \geq 1$) which were taken at different times, as noted above. By means of a trigger unit TR, the detection of movement is limited to a time window after the triggering of the shockwaves in the shockwave source SQ. In the device FK, the calculated speed values are color-coded so that the area of the patient's body PK imaged in the B-scan-images is converted to a color coded speed pattern, which is then enhanced (for example, smoothing, interpolation) in the device NV. In the mixing stage MS, the color-coded speed pattern is superimposed on the ultrasonic B-scan-image and is displayed on a video screen BS.

Figure 3:
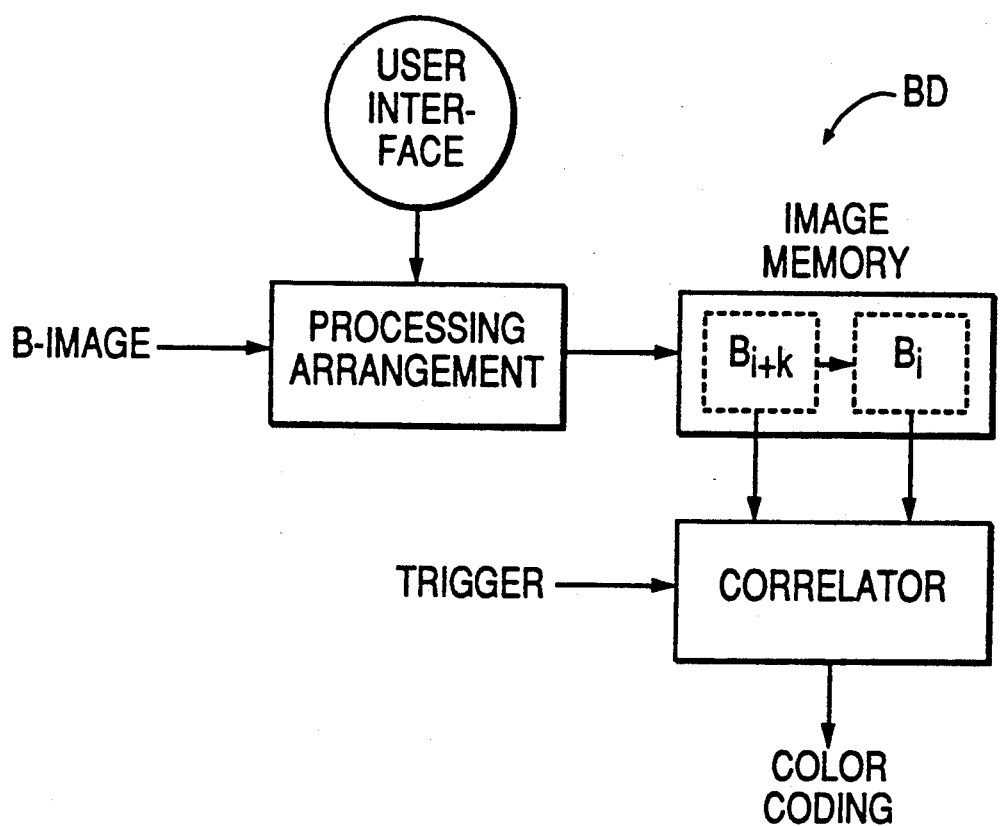
FIG. 3 is a block diagram of the element BD of FIG. 2, for the detection of motion induced by the shockwaves.

FIG. 3 is a block diagram of an embodiment of the arrangement BD (FIG. 2) for detection of the motion induced by the shockwaves. In the image memory SP, which may be, for example, a conventional previous record buffer (one b/w input, 12 bit/15 MHz A/D converter, 12 MB image memory), two successive B-scan-images $B_i$, $B_{i+k}$ ($k > 1$) are stored. By means of the processing arrangement BA, the assumed focal range within the B-scan-image—in the following also called ROI (REGION OF INTEREST)—can be determined by way of a user interface BI, so that motion is detected only within this ROI. Processing arrangement BA includes, for example, standard image processing software for defining ROI'S.

In the correlator KOR, the two ROI's (according to a, for example, square screen) are divided into image segments of the appropriate size (as a rule, several pixels). Subsequently, correlation coefficients are calculated between each segment in the first image $B_i$ and the image surroundings of the corresponding segment in the next image $B_{i+k}$, based on the grey-level values of the individual pixels. The differential vector between the segment in the first image $B_i$ and the area of maximal correlation in the next image is used to calculate the amount and speed of the movement vector. Estimated values which result from the correlation process, but are physically absurd, can be recognized and filtered out. A suitable algorithm for use in correlator KOR is as follows:

$$\text{correlation coefficient } r_{m,n} = \sum_a \sum_b P_{a,b} * Q_{a+m,b+m}$$

$r_{m,m}$: correlation coefficient between pixel a,b (coordinates a,b) in the first image and a pixel, displaced by m,n in the following image $P_{a,b}$: pixel value of the pixel a,b in the first image $Q_{a,b}$: pixel value of pixel a,b in the following image Implementation of the foregoing may be achieved by means of a standard high-speed hard-wired 2 dimensional FFT-chip.

The totality of the determined two-dimensional speed vectors are converted to a speed pattern in the subsequent color coding process. In this case, a color/intensity combination for the direction and the magnitude of movement is assigned to each image segment.

By means of the trigger unit TR, the detection of movements is limited to shock-wave relevant times. The shockwave relevant times differ by orders of magnitude from the times associated with the breathing, heartbeat frequency, or gross body movements of a patient.

In comparison to the detection of induced movement according to the Doppler method, the arrangement according to the invention has the advantage of being able to detect two-dimensional speed components. As a result, the B-scan-image of an in-line scanner as well as of an off-axis scanner can be used without any losses in the detection of motion in a possible privileged direction.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A system for locating the focal range of the shockwaves generated by a shockwave source relative to a concrement situated in the body of a living being, comprising:

an ultrasonic scanner;

an ultrasonic B-scan imaging device, coupled to the ultrasonic scanner for generating ultrasonic B-scan-images of an image area within the body, image memory means for storing said ultrasonic B-scan-images in chronological sequence;

correlating means for dividing said B-scan-images into image segments, and for correlating image segments of a first B-scan-image with a corresponding image segment of at least one subsequent B-scan-image to detect motion induced in the body by said shockwaves;

trigger means providing a signal to said correlating means that limits the detection of motion to a predetermined time window after a triggering of shockwaves;

means for generating a color-coded speed pattern of the image area in response to motion detected by said correlating means; and means for superimposing said color-coded speed pattern on the ultrasonic B-scan-images.

2. A system according to claim 1 further comprising means for determining a region of interest within the ultrasonic B-scan-image whereby motion is detected only within said region of interest.

3. A system according to claim 2 further comprising means for post processing of the color-coded speed pattern by selectively applying at least one of smoothing and interpolation.

4. A system according to claim 1 further comprising means for post-processing of the color-coded speed pattern by selectively applying at least one of smoothing and interpolation.

* * * * *